(12) United States Patent
Marten

(10) Patent No.: US 10,843,060 B2
(45) Date of Patent: Nov. 24, 2020

(54) SYSTEMS AND METHODS FOR BALL LOCATION ON A SPORTS FIELD

(71) Applicant: Dish Network L.L.C., Englewood, CO (US)

(72) Inventor: Neil Marten, Lakewood (CO)

(73) Assignee: DISH NETWORK L.L.C., Englewood, CO (US)

(*) Notice: Subject to any disclaimer, the term of this patent is extended or adjusted under 35 U.S.C. 154(b) by 0 days.

(21) Appl. No.: 16/152,220

(22) Filed: Oct. 4, 2018

(65) Prior Publication Data
US 2020/0108302 A1    Apr. 9, 2020

(51) Int. Cl.
| | | |
|---|---|---|
| A63B 71/06 | (2006.01) | |
| A63B 57/00 | (2015.01) | |
| G06K 9/00 | (2006.01) | |
| G01V 3/08 | (2006.01) | |
| G01V 1/00 | (2006.01) | |
| G01N 33/24 | (2006.01) | |

(52) U.S. Cl.
CPC .............. *A63B 71/06* (2013.01); *A63B 57/00* (2013.01); *G01N 33/246* (2013.01); *G01V 1/001* (2013.01); *G01V 3/081* (2013.01); *G06K 9/00624* (2013.01)

(58) Field of Classification Search
CPC ................................ A63B 71/06; A63B 57/00
See application file for complete search history.

(56) References Cited

U.S. PATENT DOCUMENTS

| | | | | |
|---|---|---|---|---|
| 5,912,700 A | * | 6/1999 | Honey | A63B 71/0605 348/157 |
| 6,705,942 B1 | * | 3/2004 | Crook | A63B 24/0003 463/3 |
| 7,207,902 B1 | * | 4/2007 | Hamlin | A63B 24/0021 473/353 |
| 8,989,880 B2 | * | 3/2015 | Wohl | G06K 7/10227 700/91 |
| 9,711,015 B2 | * | 7/2017 | Saboune | G06F 3/016 |
| 2005/0227791 A1 | * | 10/2005 | McCreary | A63B 69/3658 473/407 |
| 2006/0287140 A1 | * | 12/2006 | Brandt | A63B 71/0605 473/467 |
| 2009/0036237 A1 | * | 2/2009 | Nipper | A63B 24/0021 473/409 |
| 2011/0230273 A1 | * | 9/2011 | Niegowski | A43B 3/0005 473/199 |
| 2014/0274155 A1 | * | 9/2014 | Langberg | H04W 4/029 455/456.3 |

(Continued)

*Primary Examiner* — James S. McClellan
(74) *Attorney, Agent, or Firm* — Seed IP Law Group LLP

(57) ABSTRACT

Systems and methods for ball location on a sports field may include a plurality of soil moisture sensors distributed on the sports field, such as on a golf course. Each of the soil moisture sensors has a location on the sports field known to the system, and a ball detector that detects a ball being within proximity to the soil moisture sensor. This may be accomplished via one or more of a magnetometer, vibration detector and motion sensor of the soil moisture sensor. The system may use signals from the soil moisture sensors indicating such information to provide information to one or more players regarding a game score and/or other game play statistics based on the ball being within proximity to one or more particular soil moisture sensors.

19 Claims, 6 Drawing Sheets

(56) References Cited

U.S. PATENT DOCUMENTS

| | | | | |
|---|---|---|---|---|
| 2014/0297007 A1* | 10/2014 | Voutilainen | ........ | A63B 24/0003 |
| | | | | 700/91 |
| 2015/0355311 A1* | 12/2015 | O'Hagan | ................ | G01S 5/021 |
| | | | | 340/539.13 |
| 2017/0061817 A1* | 3/2017 | Mettler | ................ | G09B 19/003 |
| 2018/0348760 A1* | 12/2018 | Peverill | ................ | G05D 1/0088 |
| 2019/0217178 A1* | 7/2019 | Yun | .................... | A63B 69/3614 |

\* cited by examiner

SYSTEMS AND METHODS FOR BALL LOCATION ON A SPORTS FIELD

TECHNICAL FIELD

The disclosure relates to location systems and, particularly, to ball location on a sports field during game play.

BRIEF SUMMARY

Games such as golf may be enhanced by providing the player with the ability to easily locate, and thus track, the location and movement of the ball. For example, a current location of the player's ball may be displayed on the player's mobile device such that a player may be able to easily locate their ball on the golf course after each swing, in order to proceed with the game in a more efficient manner. Also, the player may be provided statistics regarding game play, such as driving distance, current score and distance from the ball to the hole on the golf course. Based on the ball's current location and path traveled, the player may be able to more efficiently compare and compete with other players, and improve skills and performance. Also, such statistics may be provided to facilitate other game variations, such as driving contests and "best ball" style tournaments, and other interactive and augmented games.

However, using GPS-enabled golf balls to perform ball location involves implementing costly technology and substantial interaction by the user with their mobile device, which distracts from the game. Such systems are also time-consuming, and take control away from the owner, manager or facilitator of the golf course, thus reducing opportunities for providing centrally managed game enhancements in a more efficient and less costly manner. In addition, sports facilities with large grass playing fields, such as golf courses, use large amounts of water to maintain the grass. Using soil moisture sensors enables more accurate regulation of water usage to reduce overall water consumption and environmental costs. Thus, described herein are systems and methods for ball location on a sports field, such as a golf course, that use soil moisture sensors distributed on the sports field to save costs by reducing water usage while also providing more efficient ball location.

BRIEF DESCRIPTION OF THE DRAWINGS

The components in the drawings are not necessarily to scale relative to each other. Like reference numerals designate corresponding parts throughout the several views.

DETAILED DESCRIPTION

Figure 1:
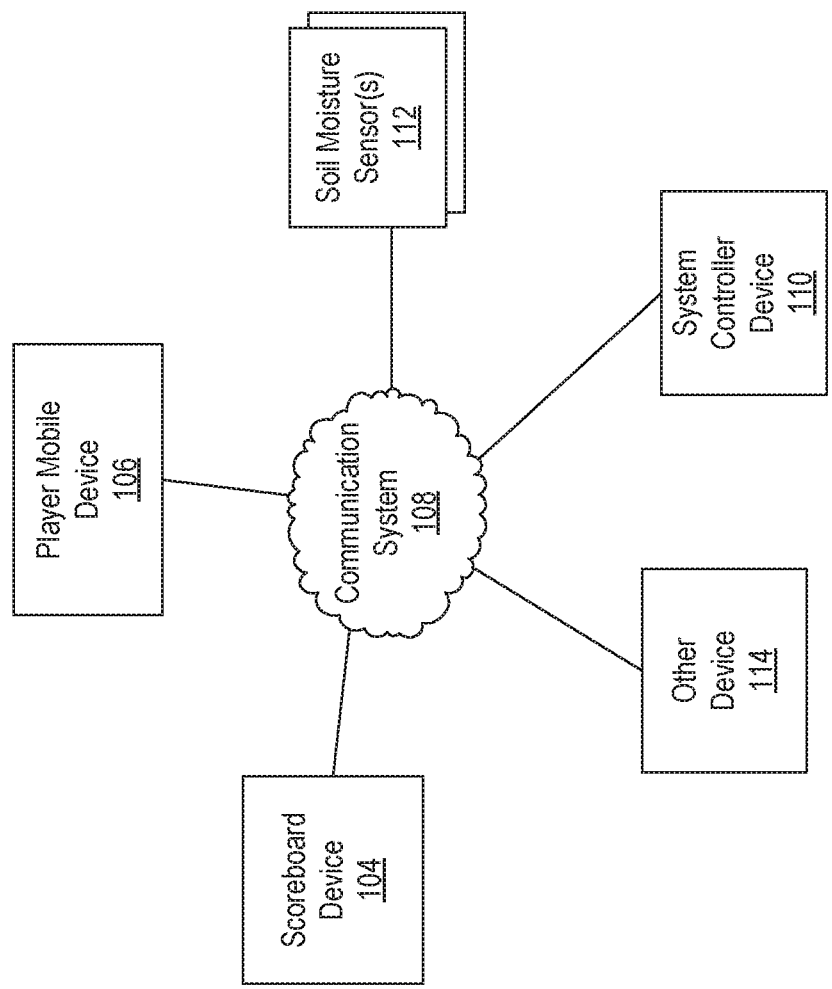
FIG. 1 is a block diagram illustrating an example environment in which embodiments of systems and methods for ball location on a sports field may be implemented, according to one example embodiment.

FIG. 1 is a block diagram illustrating an example environment 102 in which embodiments of systems and methods for ball location on a sports field may be implemented, according to one example embodiment.

Before providing additional details regarding the operation and constitution of systems and methods for ball location on a sports field, the example content environment 102, within which such systems and methods may operate, will be briefly described.

In the environment 102, a network of operable soil moisture sensors 112 is present on a grass sports field, such as a golf course, soccer field, baseball field, football field, field hockey field, etc. Overall, the term "grass sports field" as used herein includes any sports field with any amount of grass thereon, whether it covers the entire sports filed, or only one or more portions of the sports field. One or more of the soil moisture sensors 112 may be communicatively coupled directly or indirectly, such as via a communication system 108, to a system controller device 110, a player mobile device 106, a scoreboard device 104, and/or another device 114.

One or more of the soil moisture sensors 112 may interconnect to one or more communications media (such as a wireless computer network antenna, satellite antenna, telephone company switch, Ethernet portal, off-air antenna, or the like), data sources, or other devices (such as a system controller device 110, player mobile device 106, scoreboard device 104, other soil moisture sensors 112 or other device 114). The soil moisture sensors 112 measure the volumetric water content or water potential in soil, such as in the soil of golf courses, parks and other sports fields.

Further, one or more of the soil moisture sensors 112 may include user interface devices, such as buttons or switches. In many applications, a remote-control device (not shown) is operable to control the soil moisture sensors 112. The remote-control device typically communicates with the soil moisture sensor 112 using a suitable wireless medium, such as infrared ("IR"), radio frequency ("RF"), or the like.

Each of the soil moisture sensors 112 distributed on the golf course has a ball detector that detects a ball being within proximity to the soil moisture sensor. For example, this detection may be accomplished via one or more of a magnetometer, vibration detector and motion sensor of the soil moisture sensor 112. In the case of the soil moisture sensor 112 using a magnetometer, the ball will have a type of metal on the surface and/or interior of the ball that activates the magnetometer. The amount of metal in the ball is sufficient to activate the magnetometer when the ball is within a desired proximity to the soil moisture sensor 112. For example, the amount of metal on the surface and/or interior of the ball may be in an amount sufficient to activate the magnetometer when the ball is within 5 feet of the soil moisture sensor 112. Other distances, such as any falling within 1-40 feet or more, may also be selected, and the applicable amount of metal is then provided on and/or in the ball in a sufficient amount such that the magnetometer is activated when the ball is within the selected distance from the soil moisture sensor 112.

In response to the detection of the ball being within proximity to the soil moisture sensor 112, the soil moisture sensor 112 may generate a first electronic signal indicative of the ball being within proximity to the soil moisture sensor 112. The soil moisture sensor 112 may then communicate the first electronic signal indicative of the ball being within proximity to the soil moisture sensor 112. For example, the soil moisture sensor 112 may then communicate, via communication system 108, the first electronic signal indicative of the ball being within proximity to the soil moisture sensor 112 to the system controller device 110, player mobile device 106, scoreboard device 104 and/or another device 114. In one embodiment, the system controller device 110 may process this signal and/or combine such information with other data received from one or more soil moisture sensors 112, player account information, game rules, player preference information, etc., to provide information to one or more players regarding a game score and/or other game play statistics based on the ball being within proximity to a particular soil moisture sensor 112. For example, the system controller device 110 may have information regarding the locations of all the soil moisture sensors 112. These locations may be represented based on relative location to each other of the soil moisture sensors 112, and/or specific location coordinates of the soil moisture sensor in a two-dimensional (2D) or three-dimensional (3D) coordinate system. The system controller device 110 may then determine that the location of the ball is the location (or near the location) of a particular soil moisture sensor 112, based on receiving a signal from that particular soil moisture sensor 112 indicative of the ball being within proximity to that soil moisture sensor 112. The system controller device 110 may then determine a game score and/or other game play statistics based on the determined location of the ball.

As one example, the system controller device 110 may determine a distance from the golf ball on a golf course to a known location of a tee-off area, a known location of a golf hole on the golf course, and/or some other target or location on the golf course known to the system controller device 110. This information may then be used by the system controller device 110 to compile and communicate game play statistics such as driving distance and accuracy scores. The system controller device 110 may also generate a 2D or 3D rendering, or topographical map, of the golf course, and indicate on the rendering or map the corresponding determined location of the golf ball on the golf course. In some embodiments, the system controller device 110 may determine a golf score based on how many times a new location of the golf ball is determined to occur within a particular time period of game play (counting each movement of the ball over a threshold distance on the golf course as a swing that hit the golf ball).

Such information regarding game scores and game play statistics may be communicated, via communication system 108, to the scoreboard device 104, player mobile device 106 and/or other device 114, from the system controller device 110 and/or directly from one or more of the soil moisture sensors 112. The scoreboard device 104, player mobile device 106 and/or other device 114 may then present such information on a respective display of the scoreboard device 104, player mobile device 106 and/or other device 114. The scoreboard device 104 may present a graphical display of usage patterns, general course statistics and/or weekly leader board statistics based on the determined locations of players' golf balls on the golf course at particular times and triggering events; for example items such as average driving distance, total distance the ball is driven over time or per game, accuracy statistics regarding how frequently the ball lands on the fairway, how close the ball is to the fairway or other target areas, comparative statistics to other players, etc., may be presented on the scoreboard device 104, player mobile device 106 and/or other device 114.

Examples of the other device 114 may include, but are not limited to, a presentation device, a television ("TV"), a mobile device, a smartphone, a tablet device, a personal computer ("PC"), a sound system receiver, a digital video recorder ("DVR"), a digital video disc ("DVD") device, game system, or the like. The scoreboard device 104, player mobile device and/or other device 114 may employ a display, one or more speakers, and/or other output devices to communicate video and/or audio content to a user. In many implementations, the scoreboard device 104, player mobile device 106 and/or other device 114 are communicatively coupled, directly or indirectly, to the soil moisture sensor 112. Further, the system controller device 110, scoreboard device 104, player mobile device 106 and/or other device 114 may be integrated into a single device. Such a single device may have the above-described functionality of the system controller device 110, scoreboard device 104, player mobile device 106 and/or other device 114, or may even have additional functionality.

Information regarding or based on the determined location of the ball may be communicated to the system controller device 110, scoreboard device 104, player mobile device 106 and/or other device 114 from the soil moisture sensors 112 through suitable communication media, generally illustrated as communication system 108 for convenience. Communication system 108 may include many different types of communication media, now known or later developed. Non-limiting media examples include telephone systems, the Internet, internets, intranets, cable systems, fiber optic systems, microwave systems, asynchronous transfer mode ("ATM") systems, frame relay systems, digital subscriber line ("DSL") systems, radio frequency ("RF") systems, and satellite systems. Communication system 108 may include any telecommunications network, computer network, or combination of telecommunications and computer networks that enables applicable communication between the various devices connected to the communication system 108 shown in FIG. 1. For example, a communications network of communication system 108 may include a local area network that uses wireless fidelity (Wi-Fi) high frequency radio signals to transmit and receive data over distances of a few hundred feet. The local area network may be a wireless local area network (WLAN) based on the Institute of Electric and Electronic Engineers (IEEE) 802.11 standards. However, other wired and wireless communications networks and protocols may be used to link the various devices and systems shown in FIG. 1. Thus, systems shown in FIG. 1 may have various applicable wireless transmitters and receivers and, in the case of using a Wi-Fi wireless link, may also have the corresponding executable Wi-Fi compatible network communications software that initiates, controls, maintains or manages the wireless link between the systems shown in FIG. 1 and the various other devices and systems within, or communication system 108 over the Wi-Fi signal of communication system 108.

The communication system 108 may comprise connections to the systems shown in FIG. 1 that provide services to the systems shown in FIG. 1, and may itself represent multiple interconnected networks. For instance, wired and wireless enterprise-wide computer networks, intranets, extranets, and/or the Internet may be included in, or comprise a part of, communication system 108. Embodiments may include various types of communication networks including other telecommunications networks, cellular networks and other mobile networks. There may be any variety of computers, switching devices, routers, bridges, firewalls, edge devices, multiplexers, phone lines, cables, telecommunications equipment and other devices within communication system 108 and/or in the communications paths between the soil moisture sensors 112, player mobile device 106, scoreboard device 104, other device 114 and/or system controller device 110. Some or all of such equipment of communication system 108 may be owned, leased or controlled by third-party service providers.

In accordance with an aspect of the disclosure, the soil moisture sensor 112, player mobile device 106, scoreboard device 104, other device 114 and/or system controller device 110 may contain discrete functional program modules that might make use of an application programming interface (API), or other object, software, firmware and/or hardware, to request services of each other (e.g., ball location and soil moisture data services) and/or one or more of the other entities within or connected to the communication system 108.

For example, communication can be provided over a communications medium, e.g., client and server systems running on any of the soil moisture sensor 112, player mobile device 106, scoreboard device 104, other device 114 and/or system controller device 110. These client and server systems may be coupled to one another via transmission control protocol/internet protocol (TCP/IP) connection(s) for high-capacity communication. The "client" is a member of a class or group that uses the services (e.g., ball location and soil moisture data services) of another class or group to which it is not related. In computing, a client is a process, i.e., roughly a set of instructions or tasks, executed by hardware that requests a service provided by another program. Generally, the client process utilizes the requested service without having to "know" any working details about the other program or the service itself. In a client/server architecture, particularly a networked system, a client is usually a computer or device that accesses shared network resources provided by another computer or device, e.g., a server. In the example of FIG. 1, the system controller device 110 may be a client requesting the services of the soil moisture sensors 112, and the player mobile device 106, scoreboard device 104 and/or other device 114 may be clients requesting the services of the system controller device 110 and/or the soil moisture sensors 112 acting as server(s). However, any entity in FIG. 1, including the soil moisture sensors 112, player mobile device 106, scoreboard device 104, system controller device 110 and other device 114, can be considered a client, a server, or both, depending on the circumstances.

One or more cellular towers and stations may be part of a cellular network that is part of the communication system 108 and may be communicatively linked by one or more communications networks or communication mediums within the communication system 108 (e.g., using a cellular or other wired or wireless signal) in order to facilitate sending and receiving information in the form of synchronous or asynchronous data. This communication may be over a wireless signal on the cellular network of communication system 108 using applicable combinations and layers of telecommunications and networking protocols and standards such as fourth generation broadband cellular network technology (4G), Long Term Evolution (LTE), HTTP and TCP/IP, etc.

Although the physical environment of communication system 108, including the soil moisture sensor 112, player mobile device 106, scoreboard device 104, other device 114 and/or system controller device 110, may have connected devices such as computers, the physical environment may alternatively have, or be described as comprising, various digital devices such as smartphones, tablets, personal digital assistants (PDAs), televisions, MP3 players, etc.; software objects such as interfaces, Component Object Model (COM) objects; and the like.

There are a variety of systems, components, and network configurations that may also support distributed computing and/or cloud-computing environments within the communication system 108. For example, computing systems may be connected together within the communication system 108 by wired or wireless systems, by local networks or by widely distributed networks. Currently, many networks are coupled to the Internet, which provides an infrastructure for widely distributed computing, and encompasses many different networks. Any such infrastructures, whether coupled to the Internet or not, may be used in conjunction with, be connected to, or comprise part of the communication system 108.

Although not required, the embodiments will be described in the general context of computer-executable instructions, such as program application modules, objects, or macros stored on computer- or processor-readable storage media and executed by a computer or processor. Those skilled in the relevant art will appreciate that the illustrated embodiments as well as other embodiments can be practiced with other system configurations and/or other computing system configurations, including hand-held devices, multiprocessor systems, microprocessor-based or programmable consumer electronics, personal computers ("PCs"), network PCs, minicomputers, mainframe computers, and the like. The embodiments can be practiced in distributed computing environments where tasks or modules are performed by remote processing devices, which are linked through a communications network such as communication system 108. In a distributed computing environment, program modules may be located in both local and remote memory storage devices.

In at least one embodiment, the received signals from the ball detector of each soil moisture sensor 112 is converted by the soil moisture sensor 112 into a suitable signal that is ultimately communicated to the player mobile device 106, scoreboard device 104, system controller device 110 and/or other device 114. Other embodiments of the player mobile device 106, scoreboard device 104, system controller device 110 and/or other device 114 may receive such signals from soil moisture sensors 112 via locally broadcast RF signals, cable, fiber optic, Internet media, or the like.

In addition, system controller device 110 may provide various forms of content and/or services to various devices. For example, system controller device 110 may also provide information to the player mobile device 106, scoreboard device 104, and/or other device 114 including or regarding historical game play statistics, commentary, comparative game play statistics (driving distances, etc.) to other players who have played on the same hole or course (including professional players) video of game play, images of game play, images of the ball at its current location, weather data, and other sports and entertainment multimedia content. For example, the system controller device 110 may generate media, such as, for example, 3D and/or computer generated imagery (CGI) that includes highlight clips of various players' game play, which may be fully computer generated from the ball position data (without use of cameras) from the ball location manager 222. Such media may be used in the clubhouse scoreboard, such as displayed on scoreboard device 104, and/or posted on a player's YouTube channel or other social media web site, profile, account or channel automatically. In some embodiments, avatars of the players may represent the players in the videos or other generated media. The players may also or instead be represented based on statistics and photos of the player from the profile associated with the game, club or organization associated with the golf course or other sports field. In various embodiments, the media representation of the player may be linked to their social media profiles and/or photos posted on one or more social media web sites of the player with consent of the player. In this manner the content, photos and/or other relevant information from the player's social media profile, account or channel may be automatically pulled by the system controller device 110 via communication system 108 to include or otherwise use in generating the media regarding the game play of the player and the system controller device 110 may also automatically post, via communication system 108, the generated media regarding the game play of the player on the player's social media profile, account or channel. System controller device 110 may provide an electronic program guide or other menu system data or software for a user of the soil moisture sensor 112 to organize, navigate and select soil moisture levels and related information, available game play statistics that were received based on the determined location of the ball and other content.

In some embodiments, the system controller device 110 may determine that one or more of the soil moisture sensors 112 is malfunctioning and/or requires maintenance. For example, if the soil moisture sensors 112 stops communicating with the system controller device 110 over a predetermined time period or does not respond to a query from the system controller device 110, the system controller device 110 may determine that particular soil moisture sensor 112 is malfunctioning and/or requires maintenance. Also, the soil moisture sensors 112 may send the system controller device 110 a signal indicative of a malfunction or maintenance issue regarding the soil moisture sensor 112. The system controller device 110 may communicate an alert to the player mobile device 106, scoreboard device 104 and/or other device 114 regarding the a signal indicative of a malfunction or maintenance issue regarding the soil moisture sensor 112. The system controller device 110 may also or instead take other corrective actions in response to such an alert, including, but not limited to remotely activating a diagnostic test to be performed on the soil moisture sensor 112, initiating a maintenance service request or maintenance call, shutting down a portion of the sports field and/or stopping or pausing a game being played thereon.

The above description of the environment 102, and the various devices therein, is intended as a broad, non-limiting overview of an example environment in which various embodiments of systems and methods for ball location on a sports field may be implemented. FIG. 1 illustrates just one example of an environment 102, and the various embodiments discussed herein are not limited to such environments. In particular, environment 102, and the various devices therein, may contain other devices, systems and/or media not specifically described herein.

Example embodiments described herein provide applications, tools, data structures and other support to implement systems and methods for ball location on a sports field. Other embodiments of the described techniques may be used for various purposes, including, but not limited to, location of other objects on sports fields, parks, and other areas that use moisture sensors or other sensors distributed throughout the applicable area. In the following description, numerous specific details are set forth, such as data formats, program sequences, processes, and the like, in order to provide a thorough understanding of the described techniques. The embodiments described also can be practiced without some of the specific details described herein, or with other specific details, such as changes with respect to the ordering of the code flow, different code flows, and the like. Thus, the scope of the techniques and/or functions described are not limited by the particular order, selection, or decomposition of steps described with reference to any particular module, component, or routine.

Figure 2:
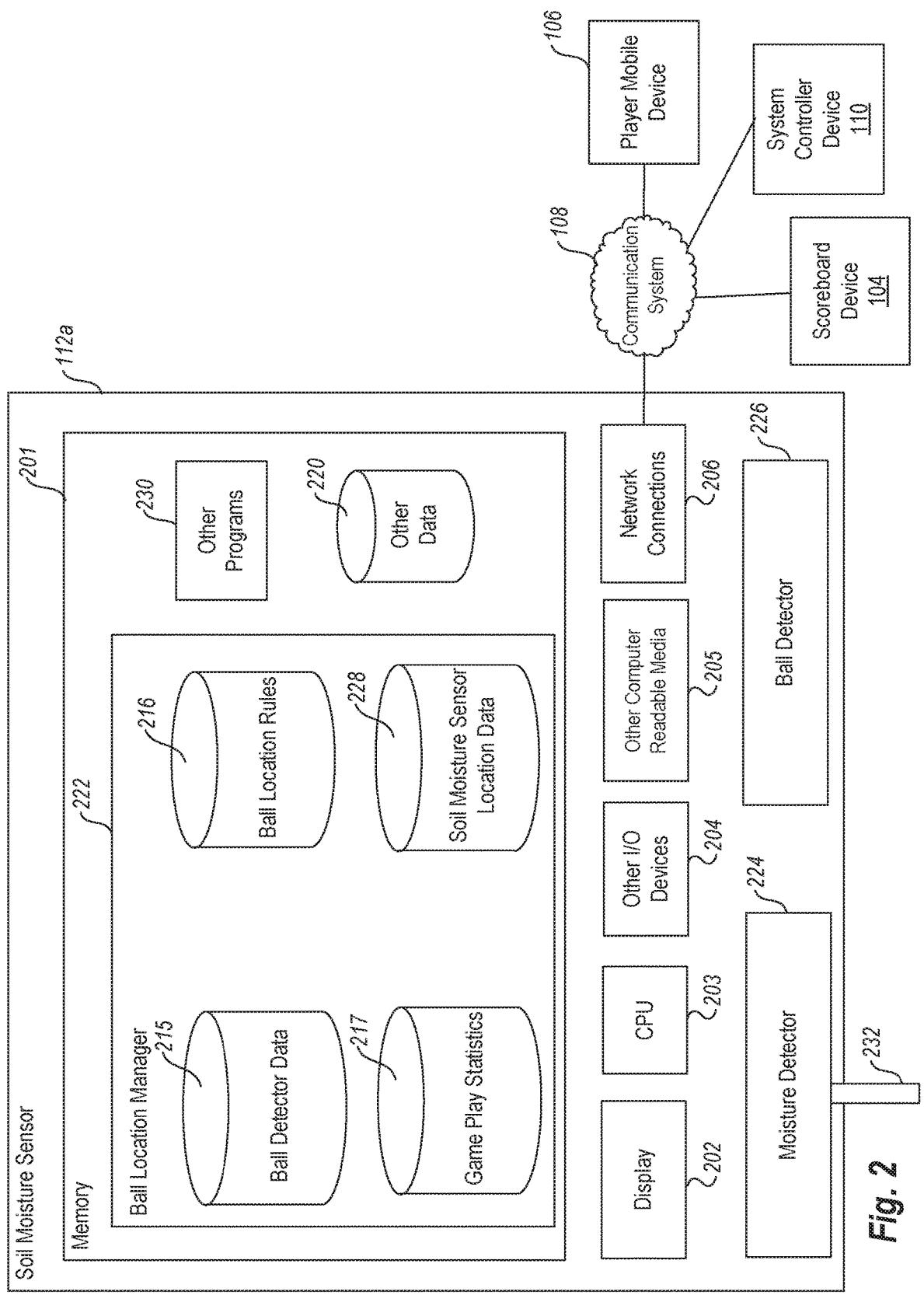
FIG. 2 is a block diagram illustrating elements of an example soil moisture sensor, according to one example embodiment.

FIG. 2 is a block diagram illustrating elements of an example soil moisture sensor 112a, according to one example embodiment.

In one embodiment, the soil moisture sensor 112 is a device that includes a moisture detector 224 coupled to one or more soil probe instruments, such as soil probe 232, that may measure the volumetric water content indirectly by using some property of the soil, such as electrical resistance, dielectric constant, or interaction with neutrons, as a proxy for the moisture content. The relation between the measured property and soil moisture is calibrated and may vary depending on environmental factors such as soil type, temperature, or electric conductivity. Reflected microwave radiation is affected by the soil moisture and may be used for remote sensing. Soil moisture sensors may refer to sensors that estimate volumetric water content. Another class of sensors measure another property of moisture in soils called water potential. These sensors are often referred to as soil water potential sensors, and include tensiometers and gypsum blocks in various embodiments. As used herein, reference to soil moisture sensors 112 also includes such sensors that measure water potential.

The soil moisture sensor 112a also includes ball detector 226. The ball detector 226 is operable to detect a ball being within proximity to the soil moisture sensor 112a. For example, this may be accomplished via one or more of a magnetometer, vibration detector and motion sensor of the ball detector 226. Note that one or more general purpose or special purpose computing systems/devices may be used to operate the soil moisture sensor 112; cause the moisture detector 224 to detect a moisture level of the grass sports field; cause the ball detector 226 to detect a ball being within proximity to the soil moisture sensor 112a; in response to the detection of the ball being within proximity to the soil moisture sensor 112a, generate a first electronic signal indicative of the ball being within proximity to the soil moisture sensor 112a; communicate the first electronic signal indicative of the ball being within proximity to the soil moisture sensor to the system controller device 110, player mobile device 106, and/or scoreboard device 104; store ball location rules in ball location rules storage 216; store ball detector data in ball detector data storage 215; store game statistics in game statistics storage 217; store soil moisture sensor location data in soil moisture sensor location data storage 228; store information regarding the soil moisture sensor 112a; store information regarding other soil moisture sensors 112 in other data storage 220; and communicate with the player mobile device 106, scoreboard device 104 and/or system controller device 110. Furthermore, each block shown may represent one or more such blocks as appropriate to a specific embodiment, or may be combined with other blocks. Also, the ball location manager 222 may be implemented in software, hardware, firmware, or in some combination to achieve the capabilities described herein.

In the embodiment shown, soil moisture sensor 112 also comprises a computer memory ("memory") 201, a display 202, one or more central processing units ("CPU") 203, input/output devices 204 (e.g., button panel, RF or infrared receiver, light emitting diode (LED) panel, liquid crystal display (LCD), USB ports, other communication ports, and the like), other computer-readable media 205, and network connections 206 (e.g., Wi-Fi interface(s), Bluetooth® interface, short range wireless interface, personal area network interface, Ethernet port(s), and/or other network ports). One or more such components that comprise the soil moisture sensor 112 may also comprise, as applicable, the one or more general purpose or special purpose computing systems/devices that may be used to operate one or more of the system controller device 110, player mobile device 106 and scoreboard device 104.

The ball location manager 222 is shown residing in memory 201. In other embodiments, some portion of the contents and some, or all, of the components of the ball location manager 222 may be stored on and/or transmitted over the other computer-readable media 205. The components of the soil moisture sensor 112 and ball location manager 222 preferably execute on one or more CPUs 203, and facilitate the receiving, decoding, processing, selecting, recording, playback and displaying of programming content one or more of the various formats described herein.

As described in more detail herein, the ball location manager 222 performs the functionality of the systems and methods for ball location on a sports field, including, but not limited to: causing the moisture detector 224 to detect a moisture level of the grass sports field; causing the ball detector 226 to detect a ball being within proximity to the soil moisture sensor 112a; in response to the detection of the ball being within proximity to the soil moisture sensor 112a, generating a first electronic signal indicative of the ball being within proximity to the soil moisture sensor 112a; communicating the first electronic signal indicative of the ball being within proximity to the soil moisture sensor to the system controller device 110, player mobile device 106, and/or scoreboard device 104; storing ball location rules in ball location rules storage 216; storing ball detector data in ball detector data storage 215; storing game statistics in game statistics storage 217; storing soil moisture sensor location data in soil moisture sensor location data storage 228; storing other information regarding the soil moisture sensor 112a in other data storage 220; storing information regarding other soil moisture sensors 112 in other data storage 220; and communicating with the player mobile device 106, scoreboard device 104 and/or system controller device 110.

For example, the ball location manager 222 may implement various ball location rules stored in ball location rules storage 216. Such ball location rules may indicate threshold values for magnetic signal strength of a ball as detected by a magnetometer of the ball detector 226, to be used to determine whether a ball is within proximity or within a "proximity zone" to the soil moisture sensor 112a, and/or magnetic field signatures of a ball as detected by a magnetometer of the ball detector 226, to be used to determine whether a ball is within proximity or within a "proximity zone" to the soil moisture sensor 112a. Other low power communication technologies, such as Bluetooth 4.0 (also referred to as Bluetooth® Low Energy or BLE) and ZigBee (with IEEE 802.15.4 as the physical network layer) may also or instead be used for proximity detection of the ball in various embodiments. When the memory 201 is that of the system controller device 110, such ball location rules in ball location rules storage 216 may also include rules for game play based on the location of the ball relative to a particular soil moisture sensor 112a as detected by the ball detector 226. For example, during the play of a golf game, the ball location rules may indicate that each time a ball is no longer detected to be within proximity of the soil moisture sensor 112a within a particular time period, and a ball is then again detected to be within proximity of the soil moisture sensor 112a during the same game within a particular time period, the detected ball is that of a different player, and thus attributes the detected location of the ball to being the location of the ball of that different player. In this manner, the system controller device 110 may collect game play statistics in game statistics storage 217 for each different player in the game (if the players swing in the same order) without having to have the ball of each player communicate a unique code, signature or identification signal to differentiate the ball from a ball of another player of in the same game. The game statistics storage 217 and/or the other data storage 220 may store data regarding historical game play statistics, commentary, comparative game play statistics (driving distances, etc.) to other players who have played on the same hole or course (including professional players), video of game play, images of game play, images of the ball at its current location and other game play data as described herein. The soil moisture sensor location data in soil moisture sensor location data storage 228 may include data indicative of the location of the soil moisture sensor 112a and/or locations of other soil moisture sensors relative to each other and/or as coordinates (e.g., GPS coordinates) in a 2D or 3D coordinate system common to the soil moisture sensors 112.

This soil moisture sensor location data may be used to determine the location on a sports field of a ball detected to be in proximity of a particular soil moisture sensor on the sports field, such as soil moisture sensor 112a. In some embodiments, more than one soil moisture sensor may detect the same ball being within proximity to the soil moisture sensor. In such a case, the ball location rules stored in the ball location rules storage 216 of the system controller device 110 may cause the system controller device 110 to determine the location of the ball on the sports field based on the strength of the signal received by the soil moisture sensor caused by the ball being within proximity to it, as compared to the strength of the signals received by one or more other soil moisture sensors caused by the ball also being within proximity those soil moisture sensors on the sports field. Such signal strength may also be used to estimate distance from each soil moisture sensor to which the ball is determined to be in proximity. The estimated distances from each soil moisture sensor to which the ball is determined to be in proximity may also be used by the system controller device 110 to triangulate the location of the ball on the sports field based on the soil moisture sensor location data communicated to the system controller device 110. In some embodiments, directional data indicative of which direction relative to a particular soil moisture sensor (such as soil moisture sensor 112a) the signal is being received may be used to facilitate determination of the ball location. For example, the soil moisture sensor 112a may have multiple signal detectors of the ball detector 226 that can detect signals received from different directions based on the location of the signal detector on the soil moisture sensor 112a.

As described herein, the ball location manager 222 may interact via the communication system 108 with other devices. For example, the other device may be a home computing system (e.g., a desktop computer, a laptop computer, mobile device, etc.) that includes or has access to (e.g., via communication system 108) the functionality of the player mobile device 106, scoreboard device 104 and/or system controller device 110.

Other code or programs 230 (e.g., an audio/video processing module, a configuration/settings manager module, a Web server, and the like), and potentially other data repositories, such as data repository 220 for storing other data (user profiles, preferences and configuration data, etc.), also reside in the memory 201, and preferably execute on one or more CPUs 203. Of note, one or more of the components in FIG. 2 may or may not be present in any specific implementation. For example, some embodiments may not provide other computer-readable media 205 or a display 202.

In some embodiments, the soil moisture sensor 112a and ball location manager 222 include an application program interface ("API") that provides programmatic access to one or more functions of the soil moisture sensor 112 and ball location manager 222. For example, such an API may provide a programmatic interface to one or more functions of the ball location manager 222 that may be invoked by one of the other programs 230, player mobile device 106, scoreboard device 104 and/or system controller device 110, or some other module. In this manner, the API may facilitate the development of third-party software, such as user interfaces, plug-ins, adapters (e.g., for integrating functions of the ball location manager 222, scoreboard device 104 and system controller device 110 into desktop and mobile applications), and the like to facilitate ball location and game play as described herein on those various connected devices.

In an example embodiment, components/modules of the soil moisture sensor 112 and ball location manager 222 are implemented using standard programming techniques. For example, the ball location manager 222 may be implemented as a "native" executable running on the CPU 203, along with one or more static or dynamic libraries. In other embodiments, the soil moisture sensor 112 and ball location manager 222 may be implemented as instructions processed by a virtual machine that executes as one of the other programs 230. In general, a range of programming languages known in the art may be employed for implementing such example embodiments, including representative implementations of various programming language paradigms, including but not limited to, object-oriented (e.g., Java, C++, C #, Visual Basic.NET, Smalltalk, and the like), functional (e.g., ML, Lisp, Scheme, and the like), procedural (e.g., C, Pascal, Ada, Modula, and the like), scripting (e.g., Perl, Ruby, Python, JavaScript, VBScript, and the like), or declarative (e.g., SQL, Prolog, and the like).

In a software or firmware implementation, instructions stored in a memory configure, when executed, one or more processors of the soil moisture sensor 112 to perform the functions of the ball location manager 222. In one embodiment, instructions cause the CPU 203 or some other processor coupled to the moisture detector 224 and ball detector 226, such as an I/O controller/processor, to cause the soil moisture sensor 112a to detect a ball being within proximity to the soil moisture sensor 112a.

The embodiments described above may also use other synchronous or asynchronous client-server computing techniques. However, the various components may be implemented using more monolithic programming techniques as well, for example, as an executable running on a single CPU computer system, or alternatively decomposed using a variety of structuring techniques known in the art, including but not limited to, multiprogramming, multithreading, client-server, or peer-to-peer, running on one or more computer systems each having one or more CPUs. Some embodiments may execute concurrently and asynchronously, and communicate using message passing techniques. Equivalent synchronous embodiments are also supported by a ball location manager 222 implementation. Also, other functions could be implemented and/or performed by each component/module, and in different orders, and by different components/modules, yet still achieve the functions of the soil moisture sensor 112 and the ball location manager 222.

In addition, programming interfaces to the data stored as part of the soil moisture sensor 112 and ball location manager 222, can be available by standard mechanisms such as through C, C++, C #, and Java APIs; libraries for accessing files, databases, or other data repositories; scripting languages such as XML; or Web servers, FTP servers, or other types of servers providing access to stored data. The ball location rules in ball location rules storage 216, ball detector data in ball detector data storage 215, game statistics in game statistics storage 217 and store soil moisture sensor location data in soil moisture sensor location data storage 228 may be implemented as one or more database systems, file systems, or any other technique for storing such information, or any combination of the above, including implementations using distributed computing techniques.

Different configurations and locations of programs and data are contemplated for use with techniques described herein. A variety of distributed computing techniques are appropriate for implementing the components of the illustrated embodiments in a distributed manner including but not limited to TCP/IP sockets, RPC, RMI, HTTP, and Web Services (XML-RPC, JAX-RPC, SOAP, and the like). Other variations are possible. Other functionality could also be provided by each component/module, or existing functionality could be distributed amongst the components/modules in different ways, yet still achieve the functions of the ball location manager 222.

Furthermore, in some embodiments, some or all of the components of the soil moisture sensor 112, the player mobile device 106, the scoreboard device 104 and the ball location manager 222 may be implemented or provided in other manners, such as at least partially in firmware and/or hardware, including, but not limited to one or more application-specific integrated circuits ("ASICs"), standard integrated circuits, controllers (e.g., by executing appropriate instructions, and including microcontrollers and/or embedded controllers), field-programmable gate arrays ("FPGAs"), complex programmable logic devices ("CPLDs"), and the like. Some or all of the system components and/or data structures may also be stored as contents (e.g., as executable or other machine-readable software instructions or structured data) on a computer-readable medium (e.g., as a hard disk; a memory; a computer network, cellular wireless network or other data transmission medium; or a portable media article to be read by an appropriate drive or via an appropriate connection, such as a DVD or flash memory device) so as to enable or configure the computer-readable medium and/or one or more associated computing systems or devices to execute or otherwise use, or provide the contents to perform, at least some of the described techniques. Some or all of the system components and data structures may also be stored as data signals (e.g., by being encoded as part of a carrier wave or included as part of an analog or digital propagated signal) on a variety of computer-readable transmission mediums, which are then transmitted, including across wireless-based and wired/cable-based mediums, and may take a variety of forms (e.g., as part of a single or multiplexed analog signal, or as multiple discrete digital packets or frames). Such computer program products may also take other forms in other embodiments. Accordingly, embodiments of this disclosure may be practiced with other computer system configurations.

Figure 3:
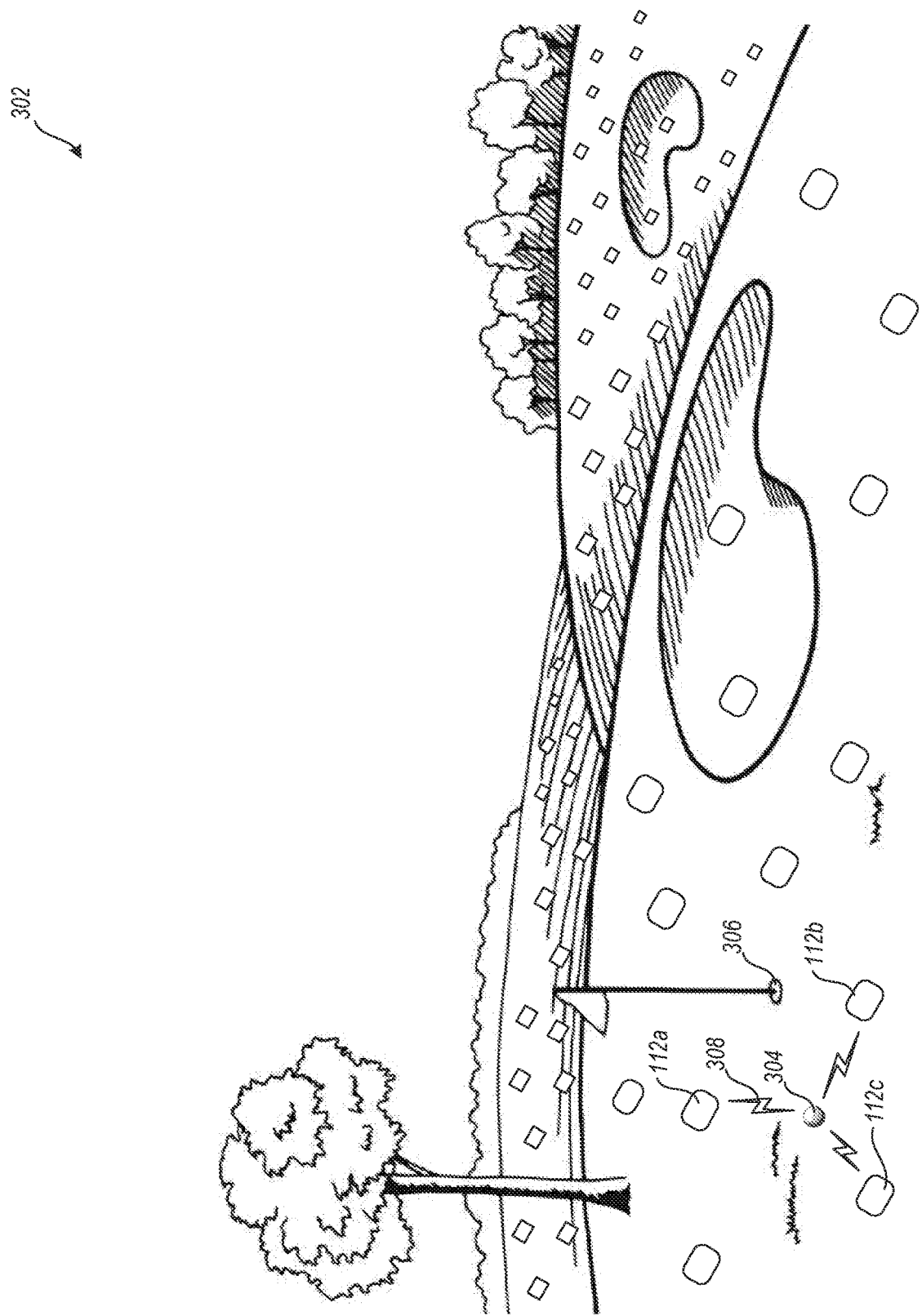
FIG. 3 is an illustration of an example golf course with a plurality of networked soil moisture sensors distributed thereon, according to one example embodiment.

FIG. 3 is an illustration of a portion of an example golf course 302 with a plurality of networked soil moisture sensors 112 distributed thereon, according to one example embodiment. The number of soil moisture sensors 112 may vary and may be fewer or more than those illustrated in FIG. 3. Generally, the larger the number of networked soil moisture sensors 112 distributed on the golf course 302, the more accurate the location of the golf ball 304 may be determined using such soil moisture sensors 112. As shown in FIG. 3, the soil moisture sensors are installed such that the top of a housing of each soil moisture sensor 112 is substantially flush or even with the ground surface of the golf course 302, such that interference with the golf ball rolling or landing on the golf course during game play is reduced. The soil moisture sensors may be in communication with one or more of a system controller device 110, scoreboard device 104 and/or player mobile device 106, such as via communication system 108 shown in FIG. 1 and FIG. 2. In some embodiments, the soil moisture sensors may be in communication with each other directly and/or via communication system 108. Each soil moisture sensor may have a unique identification number or code associated with it along with data identifying a location of the soil moisture sensor on the golf course 302. Such data may be communicated from each soil moisture sensor to one or more of the system controller device 110, the scoreboard device 104 and/or the player mobile device 106.

In the example shown in FIG. 3, during a round of golf, a golfer has hit a golf ball 304 toward the hole 306. The golf ball has landed in proximity to one or more of soil moisture sensor 112a, soil moisture sensor 112b and soil moisture sensor 112c. The known location of soil moisture sensor 112a, soil moisture sensor 112b and/or soil moisture sensor 112c may be used to determine the location on the golf course of the ball 304 detected to be in proximity of soil moisture sensor 112a, soil moisture sensor 112b and/or soil moisture sensor 112c. In some embodiments, more than one soil moisture sensor may detect the same ball being within proximity to the soil moisture sensor. For example, soil moisture sensor 112a, soil moisture sensor 112b and soil moisture sensor 112c may each detect the ball 304 to be in proximity to it. In such a case, the system controller device 110 may determine the location of the ball 304 on the golf course based on the strength of the signal 308 received by soil moisture sensor 112a caused by the ball being within proximity to it as compared to the strength of the signals received by soil moisture sensor 112b and soil moisture sensor 112c caused by the ball also being within proximity them on the golf course 302. Such signal strength may also be used to estimate distances from soil moisture sensor 112a, soil moisture sensor 112b and soil moisture sensor 112c to which the ball is determined to be in proximity. The estimated distances from soil moisture sensor 112a, soil moisture sensor 112b and soil moisture sensor 112c to which the ball is determined to be in proximity may also be used by the system controller device 110 to triangulate the location of the ball on the golf course based on the known locations of soil moisture sensor 112a, soil moisture sensor 112b and soil moisture sensor 112c communicated to the system controller device 110. In some embodiments, directional data indicative of which direction relative to a particular soil moisture sensor (such as soil moisture sensor 112a, soil moisture sensor 112b or soil moisture sensor 112c) the signal is being received may be used to facilitate determination location of the ball 304. For example, the soil moisture sensor 112a may have multiple signal detectors of the ball detector 226 that can detect signals received from different directions based on the location of the signal detector on the soil moisture sensor 112a.

Figure 4:
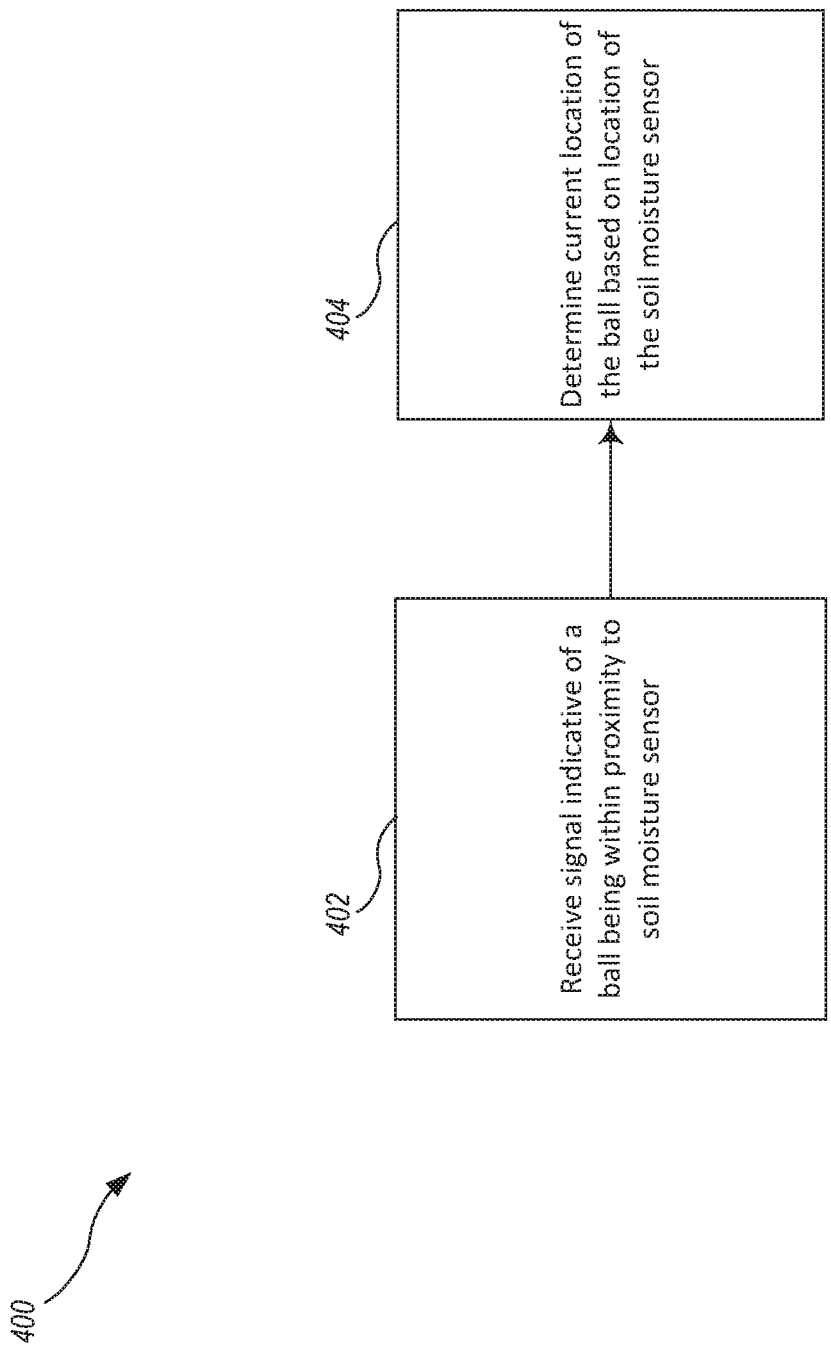
FIG. 4 is a diagram of a method for ball location on a sports field, according to an example embodiment.

FIG. 4 is a diagram of a method 400 for ball location on a sports field, according to a first example embodiment.

At 402, the system controller device 110 receives a first electronic signal from at least one of a plurality of networked soil moisture sensors distributed on a grass sports field. The first electronic signal is indicative of a ball being within proximity to the at least one of the plurality of networked soil moisture sensors.

At 404, the system controller device 110 determines a current location of the ball based on a location of the at least one of the plurality of networked soil moisture sensors and the first electronic signal indicative of the ball being within proximity to the at least one of the plurality of networked soil moisture sensors.

Figure 5:
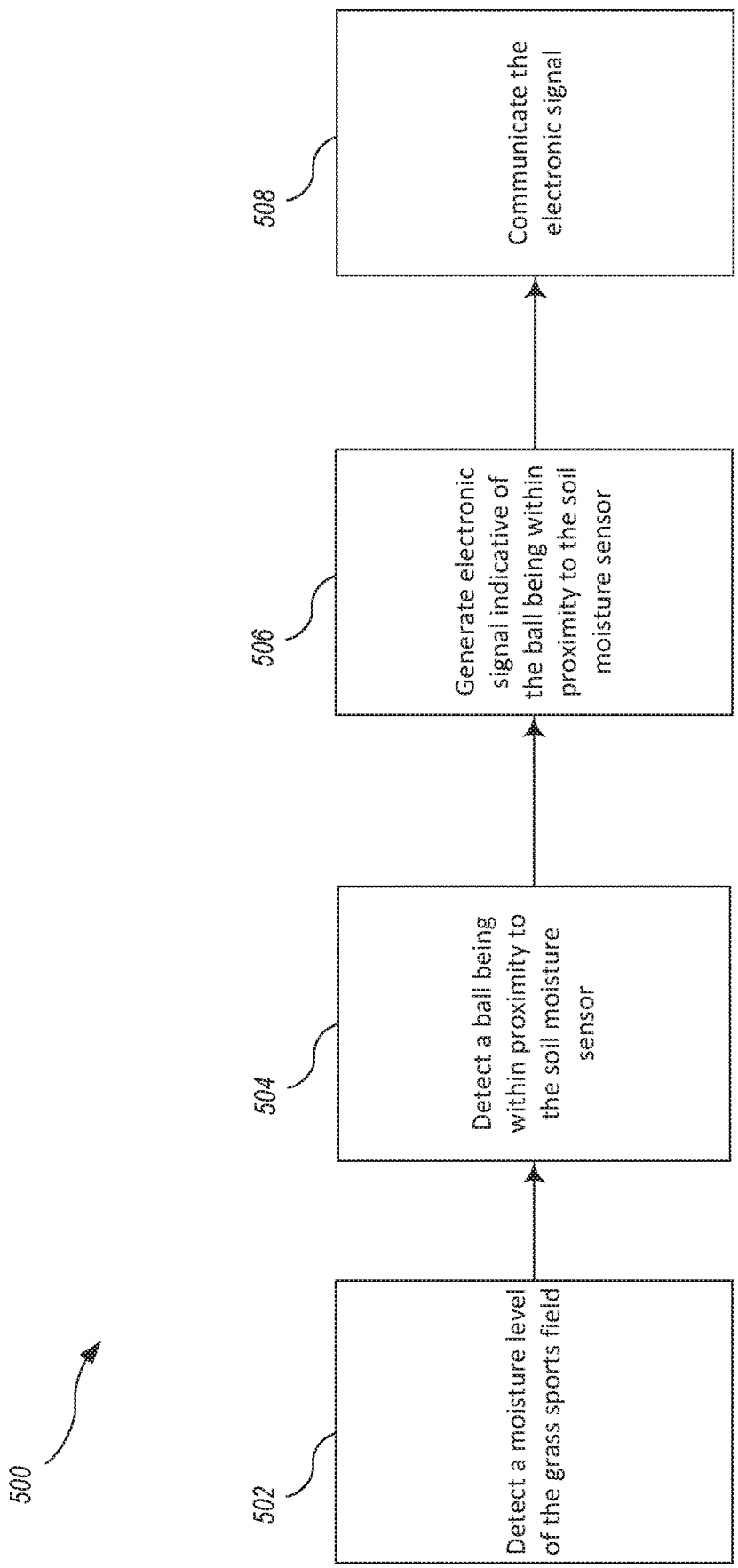
FIG. 5 is a diagram of a method of for ball location on a sports field, according to another example embodiment.

FIG. 5 is a diagram of a method 500 of for ball location on a sports field, according to another example embodiment.

At 502, the moisture detector 224 of the soil moisture sensor 112 detects a moisture level of the grass sports field.

At 504, the ball detector 226 of the soil moisture sensor 112 detects a ball being within proximity to the soil moisture sensor 112.

At 506, in response to the detection of the ball being within proximity to the soil moisture sensor 112, the soil moisture sensor 112 generates a first electronic signal indicative of the ball being within proximity to the soil moisture sensor 112.

At 508, the soil moisture sensor 112 communicates the first electronic signal indicative of the ball being within proximity to the soil moisture sensor 112 to the system controller device 110.

Figure 6:
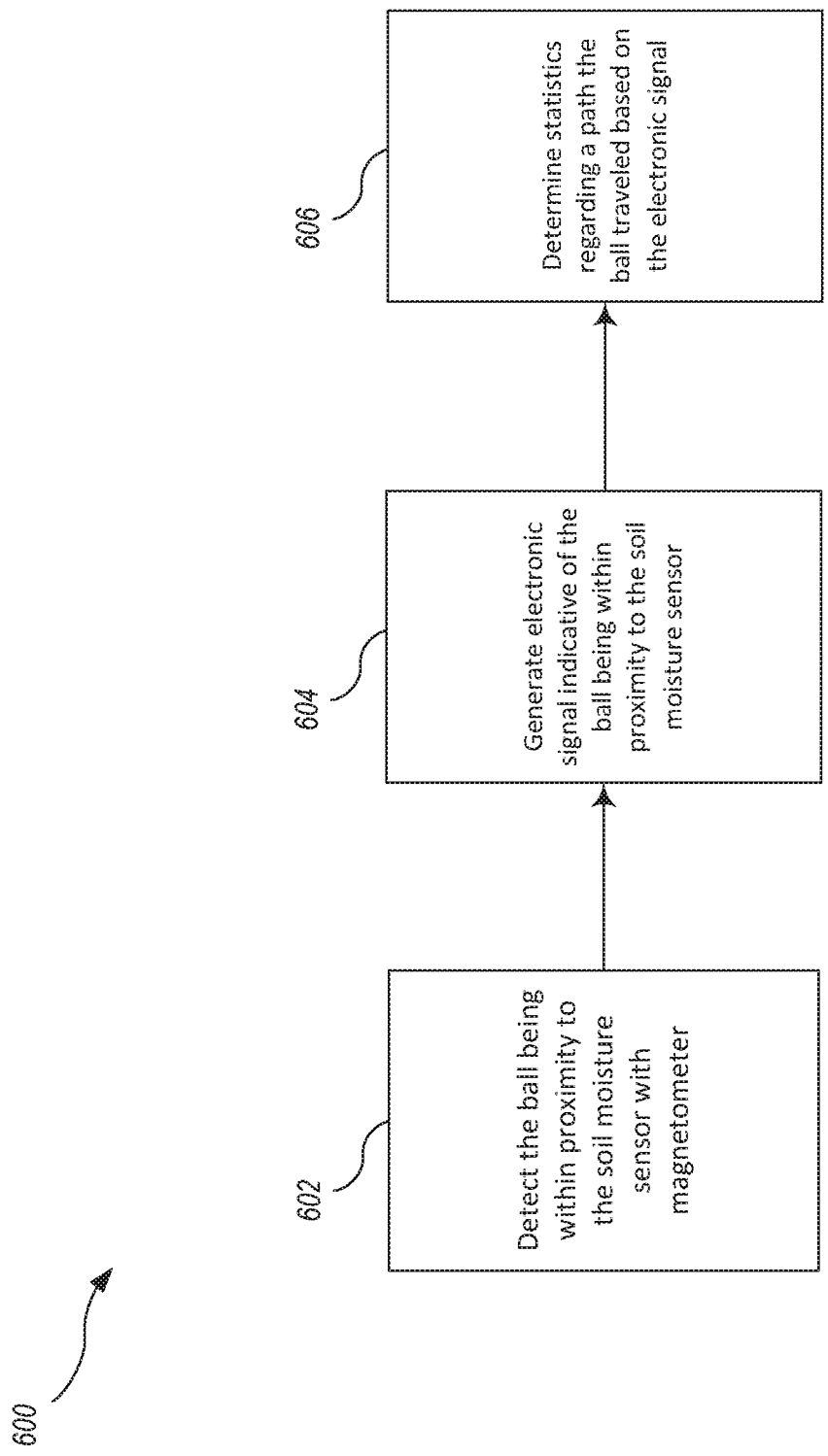
FIG. 6 is a diagram of a method determining statistics regarding a path a ball traveled on a sports field, according to an example embodiment.

FIG. 6 is a diagram of a method 600 determining statistics regarding a path a ball traveled on a sports field, according to an example embodiment.

At 602, the soil moisture sensor 112 detects the ball being within proximity to the soil moisture sensor 112 with a magnetometer. For example, the ball may have some metal detectable by the magnetometer and the magnetometer detects the ball being within proximity to the soil moisture sensor based on the magnetic field generated based on the metal.

At 604, the soil moisture sensor 112 generates the electronic signal indicative of the ball being within proximity to the soil moisture sensor 112.

At 606, the soil moisture sensor 112 determines statistics regarding a path the ball traveled based on the electronic signal. In some embodiments, the system controller device 110 may receive additional electronic signals from each soil moisture sensor of the plurality of soil moisture sensors on the sports field. The additional electronic signals may include, for each soil moisture sensor of the plurality of networked soil moisture sensors, a respective electronic signal indicative of the ball being within proximity to the soil moisture sensor. The system controller device 110 may then determine statistics regarding a path the ball traveled during a game being played on the sports field based on the received additional electronic signals from each soil moisture sensor of the plurality of soil moisture sensors. In one example embodiment, the system controller device 110 determines relative velocity and direction of a ball hit or thrown based on the speed at which the ball's magnetic signature degrades away from one or more various soil moisture sensors that the ball starts in proximity to. In this manner, soil moisture sensors downfield may be kept in a low power mode and triggered on by the system controller device 110 (or soil moisture sensor directly) when a ball is headed in what the system controller device 110 determines to be in the general direction of the soil moisture sensor.

While various embodiments have been described hereinabove, it is to be appreciated that various changes in form and detail may be made without departing from the spirit and scope of the invention(s) presently or hereafter claimed.

The invention claimed is:

1. A computer-implemented method, comprising:
   receiving, by at least one computer processor, a first electronic signal from at least one of a plurality of networked soil moisture sensors distributed on a grass sports field, the first electronic signal indicative of a ball being within proximity to the at least one of the plurality of networked soil moisture sensors, wherein the first electronic signal indicative of the ball being within proximity to the at least one of the plurality of networked soil moisture sensors is received via a magnetometer of the at least one of the plurality of networked soil moisture sensors; and
   determining, by at least one computer processor, a current location of the ball based on a location of the at least one of the plurality of networked soil moisture sensors and the first electronic signal indicative of the ball being within proximity to the at least one of the plurality of networked soil moisture sensors.

2. The method of claim 1, further comprising communicating, by at least one computer processor, information based on the determined current location of the ball to at least one of: a device associated with a player of a game being played on the grass sports field and a device associated with providing statistics regarding the game being played on the grass sports field.

3. The method of claim 1, further comprising facilitating, by at least one computer processor, game play of a game currently being played on the grass sports field based on the determined current location of the ball.

4. A computer implemented method of comprising:
   receiving, by at least one computer processor, a first electronic signal from at least one of a plurality of networked soil moisture sensors distributed on a grass sports field, the first electronic signal indicative of a ball being within proximity to the at least one of the plurality of networked soil moisture sensors, wherein the first electronic signal indicative of the ball being within proximity to the at least one of the plurality of networked soil moisture sensors is received via one or more of: a vibration detector of the at least one of the plurality of networked soil moisture sensors and a motion sensor of the at least one of the plurality of networked soil moisture sensors; and
   determining, by at least one computer processor, a current location of the ball based on a location of the at least one of the plurality of networked soil moisture sensors and the first electronic signal indicative of the ball being within proximity to the at least one of the plurality of networked soil moisture sensors.

5. The method of claim 1, further comprising:
   receiving, by at least one computer processor, a second electronic signal from the least one of the plurality of networked soil moisture sensors from which the first electronic signal indicative of the ball being within proximity to the at least one of the plurality of networked soil moisture sensors was received, the second electronic signal indicative of a moisture level of the grass sports field.

6. The method of claim 1, further comprising:
   receiving, by at least one computer processor, additional electronic signals from each soil moisture sensor of the plurality of networked soil moisture sensors, the additional electronic signals including, for each soil moisture sensor of the plurality of networked soil moisture sensors, a respective electronic signal indicative of the ball being within proximity to the soil moisture sensor; and
   determining statistics regarding a path the ball traveled during a game being played on the grass sports field based on the received additional electronic signals from each soil moisture sensor of the plurality of networked soil moisture sensors.

7. The method of claim 6, further comprising:
   determining a distance the ball traveled during a game being played on the grass sports field based on the received additional electronic signals from each soil moisture sensor of the plurality of networked soil moisture sensors using the location of the at least one of the plurality of networked soil moisture sensors and the first electronic signal indicative of the ball being within proximity to the at least one of the plurality of networked soil moisture sensors.

8. The method of claim 1, further comprising determining, by at least one computer processor, a score of a game currently being played on the grass sports field based on the determined current location of the ball using the location of the at least one of the plurality of networked soil moisture sensors and the first electronic signal indicative of the ball being within proximity to the at least one of the plurality of networked soil moisture sensors.

9. The method of claim 1, further comprising determining, by at least one computer processor, a distance from the ball to a target during a game currently being played on the grass sports field based on the determined current location of the ball using the location of the at least one of the plurality of networked soil moisture sensors and the first electronic signal indicative of the ball being within proximity to the at least one of the plurality of networked soil moisture sensors.

10. The method of claim 1 wherein the grass sports field comprises a golf course, the ball is a golf ball and further comprising:
    determining, by at least one computer processor, based on the determined current location of the golf ball using the location of the at least one of the plurality of networked soil moisture sensors and the first electronic signal indicative of the golf ball being within proximity to the at least one of the plurality of networked soil moisture sensors, one or more of: a driving distance of the golf ball; a location of the golf ball on the golf course; whether the golf ball is on a fairway of the golf course; whether the golf ball is on a putting green of the golf course; distance from the golf ball to a hole on the golf course; identification of the golf ball from a plurality of golf balls on the golf course; a golf score of a golfer associated with the golf ball; which hole on the golf course the golf ball is nearest; and which golf ball of a plurality of golf balls on the golf course is closest to a hole on the golf course.

11. A system for ball location on a grass sports field, comprising:
    a system controller device; and
    a plurality of networked soil moisture sensors distributed on the grass sports field in operable communication with the system controller device, each soil moisture sensor of the plurality of networked soil moisture sensors comprising:

at least one processor;

at least one moisture detector coupled to the at least one processor;

a ball detector coupled to the at least one processor; and at least one memory coupled to the at least one processor, the at least one memory having computer-executable instructions stored thereon that, when executed by the at least one processor, cause the at least one processor to:

cause the moisture detector to detect a moisture level of the grass sports field;

cause the ball detector to detect a ball being within proximity to the soil moisture sensor;

in response to the detection of the ball being within proximity to the soil moisture sensor, generate a first electronic signal indicative of the ball being within proximity to the soil moisture sensor; and communicate the first electronic signal indicative of the ball being within proximity to the soil moisture sensor to the system controller device, wherein the ball detector comprises a magnetometer, the ball has some metal detectable by the magnetometer and the computer-executable instructions, when executed by the at least one processor, cause the at least one processor to:

cause the magnetometer to detect the ball being within proximity to the soil moisture sensor.

12. The system of claim 11 wherein the ball detector comprises a vibration detector and the computer-executable instructions, when executed by the at least one processor, cause the at least one processor to:

cause the vibration detector to detect the ball having landed within proximity to the soil moisture sensor.

13. The system of claim 11 wherein the ball detector comprises a motion sensor and the computer-executable instructions, when executed by the at least one processor, cause the at least one processor to:

cause the motion sensor to detect the ball having passed by or landed in proximity to the soil moisture sensor.

14. The system of claim 11 wherein the ball detector comprises a camera and the computer-executable instructions, when executed by the at least one processor, cause the at least one processor to:

cause the camera to capture an object being in proximity to the soil moisture sensor; and perform object recognition identifying the object as being the ball in proximity to the soil moisture sensor.

15. The system of claim 11 wherein the ball detector comprises a camera and the computer-executable instructions, when executed by the at least one processor, cause the at least one processor to:

cause the camera to capture an image of an object being in proximity to the soil moisture sensor; and send the image of the object to the system controller device to perform object recognition identifying the object as being the ball in proximity to the soil moisture sensor.

16. The system of claim 11 wherein the ball detector comprises a camera and the computer-executable instructions, when executed by the at least one processor, cause the at least one processor to:

generate a second electronic signal indicative of the detected moisture level of the grass sports field; and communicate to the system controller device the second electronic signal indicative of the detected moisture level of the grass sports field.

17. A non-transitory computer-readable storage medium having computer executable instructions thereon, that when executed by at least one computer processor, cause the following to be performed:

cause a soil moisture sensor to detect a moisture level of a grass sports field;

cause a magnetometer of the soil moisture sensor to detect a ball being within proximity to the soil moisture sensor;

in response to the detection of the ball being within proximity to the soil moisture sensor, generate a first electronic signal indicative of the ball being within proximity to the soil moisture sensor; and communicate the first electronic signal indicative of the ball being within proximity to the soil moisture sensor.

18. The non-transitory computer-readable storage medium of claim 17 wherein the computer-executable instructions, when executed by the at least one computer processor, further cause the at least one computer processor to:

receive at the soil moisture sensor one or more additional electronic signals indicative of the ball being within proximity to one or more other soil moisture sensors; and determine statistics regarding a path the ball traveled during a game being played on the grass sports field based on the one or more additional electronic signals indicative of the ball being within proximity to the one or more other soil moisture sensors.

19. The non-transitory computer-readable storage medium of claim 17 wherein the computer-executable instructions, when executed by the at least one computer processor, cause the at least one computer processor to:

cause a vibration detector of the soil moisture sensor to detect the ball being within proximity to the soil moisture sensor.

* * * * *